| (12) United States Patent | (10) Patent No.: US 9,861,324 B2 |
| Wang et al. | (45) Date of Patent: Jan. 9, 2018 |

(54) HYBRID DETECTOR MODULES AND DYNAMIC THRESHOLDING FOR SPECTRAL CT

(71) Applicant: Virginia Tech Intellectual Properties, Inc., Blacksburg, VA (US)

(72) Inventors: Ge Wang, Latham, NY (US); Jiyang Chu, Ann Arbor, MI (US); Wenxiang Cong, Albany, NY (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 14/786,290

(22) PCT Filed: Apr. 23, 2014

(86) PCT No.: PCT/US2014/035131
§ 371 (c)(1),
(2) Date: Oct. 22, 2015

(87) PCT Pub. No.: WO2014/176328
PCT Pub. Date: Oct. 30, 2014

(65) Prior Publication Data
US 2016/0128650 A1 May 12, 2016

Related U.S. Application Data

(60) Provisional application No. 61/814,867, filed on Apr. 23, 2013.

(51) Int. Cl.
*A61B 6/00* (2006.01)
*A61B 6/03* (2006.01)
*G06T 11/00* (2006.01)

(52) U.S. Cl.
CPC ............ *A61B 6/032* (2013.01); *A61B 6/4241* (2013.01); *A61B 6/482* (2013.01); *A61B 6/5205* (2013.01);
(Continued)

(58) Field of Classification Search
CPC ..... A61B 6/032; A61B 6/4233; A61B 6/4241; A61B 6/482; A61B 6/503; A61B 6/5205; A61B 6/54; G06T 11/005; G06T 2211/408
See application file for complete search history.

(56) References Cited

U.S. PATENT DOCUMENTS 7,372,934 B2   5/2008   De Mann et al.
7,885,372 B2   2/2011   Edic et al.
(Continued)

OTHER PUBLICATIONS

Wang et al; Material Separation in X-Ray CT with energy Resolved Photon-Counting Detectors, Medical Physics, vol. 38, No. 3, Mar. 2011 [Retrieved Jul. 6, 2014]; Retrieved from http://www.ncbLnlm.nih.gov/pmc/articiesJPMC3060934/pdf/MPhy   A6-000038-001534_1.pdf; pp. 1534-1546.
(Continued)

*Primary Examiner* — Dani Fox
(74) *Attorney, Agent, or Firm* — Keith A. Vogt; Vogt IP

(57) ABSTRACT

A system and method that comprises an X-ray source configured to emit an X-ray beam; an object positioned to receive the X-ray beam; a detector configured to receive an attenuated beam of the X-rays through the object for measuring projection data from various orientations that can be used to generate spectral images in terms of energy-dependent linear attenuation coefficients, and a detector, as described above, comprising one or more energy-integrating detector elements and one or more photon counting detector elements in one or more detectors array or separate detector arrays. The photon counting detector elements may also use dynamic thresholds to define energy windows.

21 Claims, 13 Drawing Sheets

(52) U.S. Cl.
CPC ........... *G06T 11/005* (2013.01); *A61B 6/4233* (2013.01); *A61B 6/503* (2013.01); *A61B 6/54* (2013.01); *G06T 2211/408* (2013.01)

(56) References Cited

U.S. PATENT DOCUMENTS

| | | |
|---|---|---|
| 7,956,332 B2 | 6/2011 | Burr et al. |
| 2012/0265050 A1 | 10/2012 | Wang |

OTHER PUBLICATIONS

United States International Searching Authority; International Search Report & Written Opinion for PCT/US2014/034131; Aug. 29, 2014; 15 pages; Alexandria, VA; US.

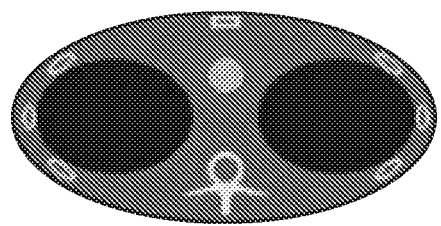
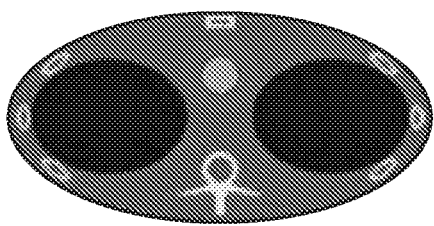
FIG. 10A  FIG. 10B
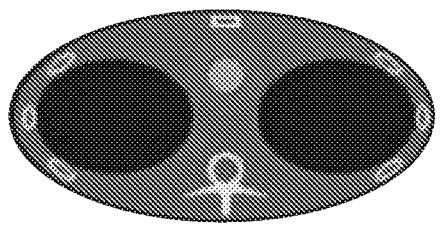
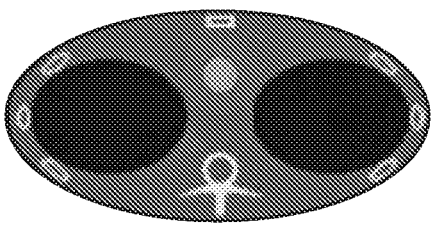
FIG. 10C  FIG. 10D
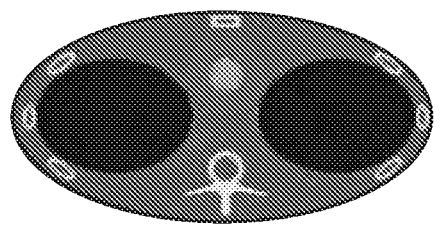
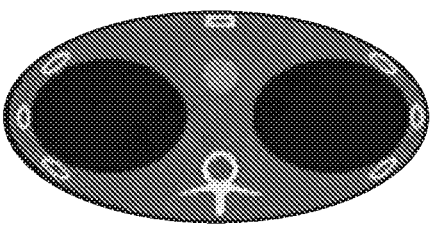
FIG. 10E  FIG. 10F Original Phantom Images in 8 Energy Windows Reconstructed Spectral Components with 3-Window Detectors

HYBRID DETECTOR MODULES AND DYNAMIC THRESHOLDING FOR SPECTRAL CT

CROSS-REFERENCE TO RELATED APPLICATIONS

This application claims the benefit U.S. Provisional Application No. 61/814,867, filed Apr. 23, 2013 and herein incorporated by reference.

STATEMENT REGARDING FEDERALLY SPONSORED RESEARCH OR DEVELOPMENT

This invention was made with government support under Grant No. R01 HL098912 awarded by the National Institutes of Health. The government has certain rights in the invention.

INCORPORATION-BY-REFERENCE OF MATERIAL SUBMITTED ON A COMPACT DISC

Not Applicable.

BACKGROUND OF THE INVENTION

Field of the Invention

The present application concerns the field of spectral computed tomography (CT). It also relates to the detection of x-rays and other radiation for applications in which it is desirable to obtain information regarding the energy of the detected radiation. The present invention also has applications in medical imaging, non-destructive testing and analysis, security applications, and other applications where energy discrimination capabilities are useful.

The attenuation properties of matter for x-rays are both energy and material dependent. At present, the x-ray detection technology is based on energy-integration in which electrical. signals, from interactions between x-ray photons and the scintillator, are accumulated over the entire energy spectrum, ignoring photon spectral information.

Traditional CT systems provided image data representative of the x-ray attenuation of an object under examination. These systems are limited in the ability to provide information about the material composition of the object, the color of the object and are costly to construct and configure.

One way to obtain information is to measure the energy of the detected radiation through the use of photon counting, detectors. Exemplary photon counting detectors include scintillator-based detectors such as those based on lutetium orthosilicate, bismuth germanate and sodium iodide together with photodetectors such as photodiodes or photomultiplier tubes. Still other scintillator materials such as lanthanum bromide are also known. Cadmium zinc telluride (CZT) based detectors are an example of direct conversion photon counting detectors.

The advantages of photon-counting detectors are evident relative to current-integrating (also referred to as energy-integrating or sometimes photon-integrating) counterparts. First, the photon-discriminating capability reveals spectral responses of materials that are invisible to the current-integrating process. In current-integrating detectors, low-energy photons carry more contrast information but receive lower weights due to beam hardening. Photon-counting detectors typically do not have such a weighting bias. Photon-counting detectors can reveal elemental composition of materials by K-edge imaging, support novel contrast-enhanced studies and have other uses for functional, cellular and molecular imaging. Further, photon-counting detectors have an inherently higher signal-to-noise ratio (SNR) by utilizing spectral information.

Photon counting techniques, however, are not without limitations. For example, the technique is not particularly suited for use over the count rates and input dynamic ranges typically encountered in CT and other x-ray applications. One technique for addressing this issue is described in Kraft, et al., *Counting and Integrating Readout for Direct Conversion X-ray Imaging Concept, Realization anti First Prototype Measurements*, 2005 IEEE Nuclear Science Symposium Conference Record, which discloses a counting and integrating pixel (CIX) structure for use with CZT detectors. A photon counter counts the photons received by a detector pixel during a reading period. An integrator simultaneously integrates the total signal current over the reading period. The described technique claims to extend the available dynamic range beyond the limits of photon counting and integration techniques taken individually, and also yields spectral information in terms of mean photon energy in the region where the operating ranges of the photon counting and integration regimes overlap.

U.S. Pat. No. 7,885,372 discloses an energy-sensitive computed tomography system that includes a detector configured to receive a transmitted beam of the X-rays that works in conjunction with a filter. The filter uses an alternating pattern of multiple attenuating materials disposed between the X-ray source and the detector to facilitate measuring projection data that can be used to generate both low-energy and high-energy spectral information.

Other solutions are set forth in U.S. Pat. No. 7,894,576 which provides an x-ray sensitive detector element which generates a time varying signal in response to x-ray photons received by the detector element, a photon counter which counts x-ray photons received by the detector element during a reading period, and a photon energy determiner which measures a total energy of the counted x-ray photons. The photon energy determiner measures a change in the detector signal during each of a plurality of sub-periods of the reading period.

Other advancement in the area of energy-discriminative photon-counting x-ray detectioninclude photon-counting detectors known as the Medipix developed by CERN (European Organization for Nuclear Research), Medipix-2 is a photon-counting readout ASIC, each element has a pixel size of 55×55 µm². The performance of Medipix-2 is limited by charge sharing over neighboring pixels, compromising energy resolution. Medipix-3.0 is a photon-processing chip. It has circuitry for each pixel and allows charge deposition to be analyzed. The readout logic supports eight energy thresholds over 110×110 µm². Sensor materials can be Si, GaAs or CdTe for preclinical and clinical x-ray imaging, respectively. The photon-counting detectors with multiple channels can be used to differentiate the attenuation characteristics of various materials.

Statistical reconstruction methods have also been developed to account for the polychromatic characteristics of x-ray photon-integrated signals in the image reconstruction process. A penalized weighted least squares (PWLS) algorithm has recently been studied for polychromatic energy-differentiated x-ray CT. Also, studies have shown that photon-counting spectral CT, as compared to conventional CT, outperforms conventional CT in contrast enhanced scans with iodine, gadolinium, and other known contrasts.

BRIEF SUMMARY OF THE INVENTION

The present invention addresses the above problems and improves upon the current designs described above. In accordance with one embodiment of the present invention, the invention combines traditional energy-integrating detector elements and Photon counting detector elements in the same detection array or module. In another aspect, the present invention provides a hybrid detector with simultaneous energy-integration and photon counting modes using dynamic thresholds.

In another embodiment, a CT detector array is provided that uses current-integrating/photon-counting, elements or modules in an interlacing fashion that synergistically combines and utilizes the strengths of each detector type. Grayscale detector modules are used to acquire regular raw data in a large dynamic range cost-effectively. In addition, spectral detector modules are used to sense energy-discriminative data in multiple energy bins. The apertures for current-integrating and photon-counting detectors may be different to compensate for different counting rates due to the different working principles of these two types of detectors.

The invention has a real value for emerging CT applications in terms of cost-effectiveness and enhanced versatility. Also disclosed is a design of a spectral detector with a dynamically changing threshold setting. In contrast to the current spectral design methods in which the energy windows are pre-fixed for all detector elements over the period of spectral imaging, the present invention provides a spatial and/or temporal variation of the energy windows defined by voltage thresholds. Utilizing compressive sensing methods allows for the recovery of full spectral information from spectral data collected via the dynamically changing or spatially randomized thresholds. By doing so, dual or triple energy windows may cover the same amount of information as what can be done with more energy windows such as 8 energy windows.

BRIEF DESCRIPTION OF THE SEVERAL VIEWS OF THE DRAWINGS

FIG. 76 shows a reconstructed image from noise-free data at Pr=11.

FIG. 10A shows the original image.

FIG. 10B shows a reconstructed image from noise-free data at Pr=1.

FIG. 10C shows a reconstructed image from noise-free data at Pr=3.

FIG. 10D shows a reconstructed image from noise-free data at Pr=5.

FIG. 10E shows a reconstructed image from noise-free data at Pr=7.

FIG. 10F shows a reconstructed image from noise-free data at Pr=9.

DETAILED DESCRIPTION OF THE INVENTION

This description is not to be taken in a limiting sense, but is made merely for the purpose of illustrating the general principles of the invention. The scope of the invention is defined by the appended claims. In a preferred embodiment, as shown in FIGS. 1A-1D, the present invention includes an integrated grayscale and spectral detector elements or modules configured as a single detector array. In addition, the invention contemplates the use of one or more arrays.

As shown, current-integrating detectors 100 and photon-counting detectors 102 may be interlaced in various patterns within the same detector array. The detectors may be arranged into an energy-sensitive or spectral computed tomography system, that comprises an X-ray source configured to emit an X-ray beam, an object positioned to receive the X-ray beam and a detector, comprising one or more arrays, configured to receive an attenuated beam of the X-rays through the object for measuring projection data from various orientations that can be used to generate spectral images in terms of energy-dependent linear attenuation coefficients. As stated above, the detector comprises one or more energy-integrating detector elements and one or more photon counting detector elements in the same detector array or separate detector arrays.

To solve any associated flux-matching problems, one solution presented by one embodiment of the invention places the attenuators in front of the spectral elements. Another approach covered by the invention is to use a smaller spectral detection aperture so that the number of photons reaching a given spectral element can be reduced. For this configuration, only a relatively small fraction of conventional detector elements are replaced by spectral elements. Hence, the cost to construct the device will be lower and at the same time the device will have the ability to acquire both grayscale and spectral information. As discussed in further detail helms, there is an optimal ratio between the number of spectral elements and the number of grayscale elements for which the hybrid detector array will perform as well as a full-width spectral detector array.

Figure 1:
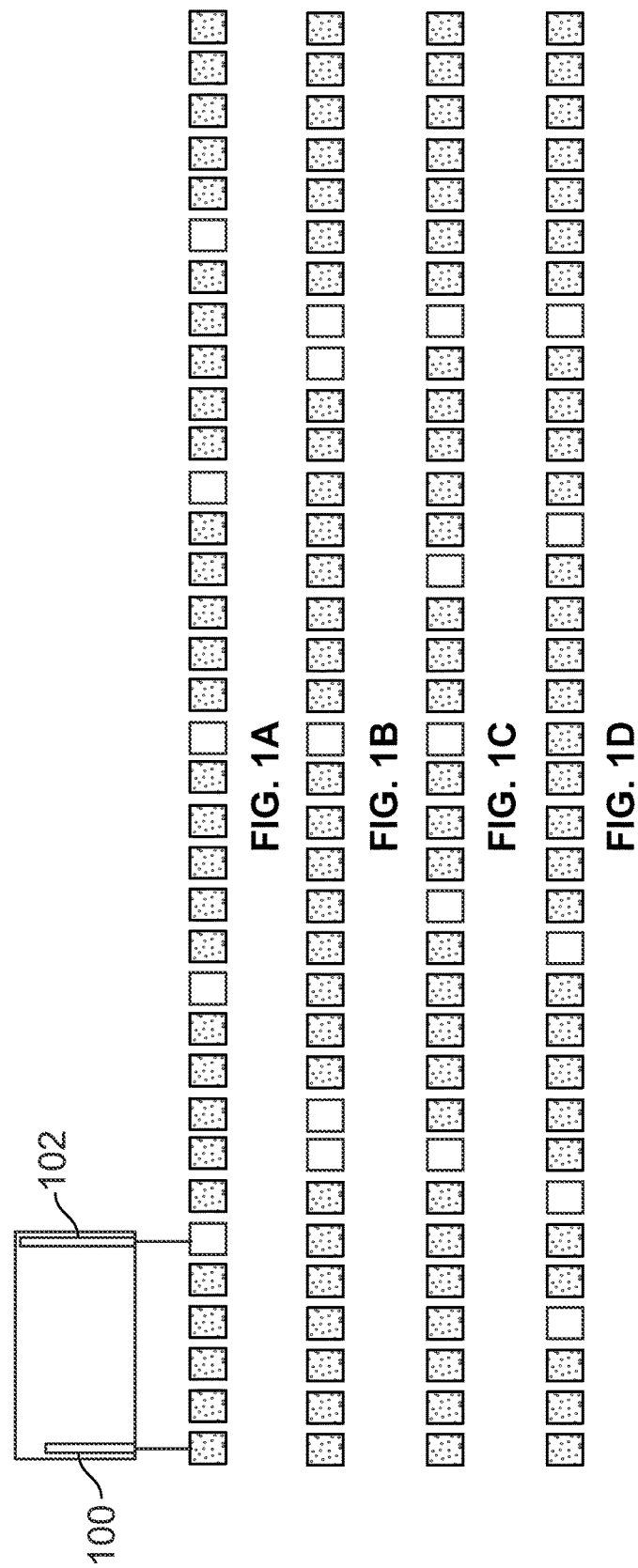
FIG. 1A schematically illustrates a hybrid detector array where stippled elements denote grayscale detector elements and white elements denote spectral detector elements respectively arranged in an evenly alternating pattern.
FIG. 1B illustrates a hybrid detector with merged spectral elements.
FIG. 1C illustrates a hybrid detector arranged such that the spectral elements are centralized.
FIG. 1D illustrates a hybrid detector arranged such that the spectral elementsare randomly arranged.

For geometrical symmetry, an evenly alternating pattern may be used to form a hybrid detector array as shown in FIG. 1A. The optimization parameters should include the ratio of the number of grayscale modules over the number of the spectral detector modules, the number of detector elements in each module, and others. A parameter to be considered is the ratio between the total number of grayscale elements and the total number of spectral elements because it determines the amount of spectral information and the cost of the hybrid detector array.

Another characteristic is the arrangement of spectral elements for a given ratio Pr. An evenly alternating pattern is illustrated in FIG. 1A. Variants are illustrated in FIGS. 1B-1D. FIG. 1B illustrates a hybrid detector with merged spectral elements. FIG. 1C illustrates a hybrid detector arranged such that the spectral elements are centralized. FIG. 1D illustrates a hybrid detector arranged such that the spectral elements are randomly arranged.

When a monochromatic x-ray beam passes through an object, the x-ray intensity attenuation obeys the Beer-Lambert law $$I(E) = I_0(E)\exp\left(-\int_{y_0}^{y_1} \mu(y, E)\,dy\right) \quad (1)$$

where $I_0(E)$ is the blank intensity for the x-ray energy level E on the spectral detector without any object in the beam, and $\mu(y,E)$ is the linear attenuation coefficient for an energy level E on a position y. A conventional grayscale detector accumulates all photons over an entire energy spectrum, and reports the reading as $$I_{gray} = \int_0^{EM} I_0(E)\exp\left(-\int_{y_0}^{y_1} \mu(y, E)\,dy\right) dE \quad (2)$$

where EM is the maximum energy. After discretization for the inner integration, we have $$\int_{y_0}^{y_1} \mu(y, E)\,dy = \sum_{i=1}^{N} w_i \mu_i(E) \quad (3)$$

where $w_i$ is the weighting factor accounting for the imaging geometry, and $\mu_i(E)$ is the linear attenuation coefficient of a pixel at energy E. Inserting Eq. (3) into Eq. (1), provides $$I(E) = I_u(E)\exp\left(-\sum_{i=1}^{N} w_i \mu_i(E)\right) \quad (4)$$

If the whole spectral range of x-rays is discretized into multiple bins $E_j$, j=1, 2 ... EM, then the grayscale measurement can be expressed as $$I_{gray} = \sum_{j=1}^{EM} Q_j J_0(E_j)\exp\left(-\sum_{i=1}^{N} w_i \mu_i(E_j)\right) \quad (5)$$

where $Q_j$ is a weighting factor, or the energy-dependent detector response. For conventional grayscale CT, the measured intensity on a detector is explained by an effective attenuation coefficient distribution, which is $$I_{gray} = I\exp\left(-\sum_{i=1}^{N} w_i \bar{\mu}_i\right) \quad (6)$$

where I is the blank intensity reading on the grayscale detector without any object in the beam. That is, $$I = \sum_{j=1}^{EM} Q_j I_0(E_j) \quad (7)$$

From Equations (5), (6), and (7), the following is obtained $$I = \sum_{j=1}^{EM} Q_j I_0(E_j)\exp\left(-\sum_{i=1}^{N} w_i[\mu_i(E_j) - \bar{\mu}_i]\right) \quad (8)$$

As the difference $\mu_i(E_j) - \bar{\mu}_i$ is very small compared to the attenuation coefficients when an object is relatively small or weakly attenuating, Eq. (8) can be approximated as $$I = \sum_{j=1}^{EM} Q_j I_0(E_j)\left\{1 - \sum_{i=1}^{N} w_i[\mu_i(E_j) - \bar{\mu}_i]\right\} \quad (9)$$

Then, with Eq. (6) we have $$\sum_{i=1}^{N} w_i\left[\sum_{j=1}^{EM} Q_j I_0(E_j)\mu_i(E_j)\right] = I\ln\left(\frac{I}{I_{gray}}\right) \quad (10)$$

which can be written in the matrix form $$A\left[\sum_{j=1}^{EM} G_j \mu(E_j)\right] = Y_0 \quad (11)$$

where A is the system matrix, µ($E_j$) is a vector which consists of spectral dependent coefficients) $\mu_t(E_j)$ at energy $E_j$, $G_j = Q_j I_0(E_j)$ and $Y_0$ contains data I ln $$\left(\frac{I}{I_{gray}}\right)$$

computed from measured grayscale data.

Eq. (11) gives a linear relationship between the spectral dependent coefficients and the grayscale data.

For another embodiment of the invention, the below linear model may be used for the reconstruction of the spectral dependent attenuation coefficients. In addition, other solutions known to those of skill in the art may be used as well. For projection data measured with spectral detectors, Eq. (11) can be converted to the following, linear system $$A\mu(E_j) = Y_j, j = 1, 2, \ldots, EM \quad (12)$$

where µ($E_j$) is the attenuation coefficient in the j-th energy bin, and $Y_j = \ln(I_0(E_j)/I(E_j))$ is the sinogram in the j-th energy bin.

According to one embodiment of the present invention, the grayscale and spectral detector elements may be integrated into a single full-width detector array, making for differences in the system matrixes for grayscale data and spectral data. Denoting the systems matrix for grayscale data as $A_G$ and the system matrix for spectral data as $A_C$, the image reconstruction for spectral CT earn be formulated as the following optimization problem $$\min_{\mu(E_j)} \begin{bmatrix} \sum_{j=1}^{EM} c_j \|A_c \mu(E_j) - Y_j\|^2 + \\ c_0 \left\|A_c\left(\sum_{j=1}^{EM} G_j \mu(E_j)\right) - Y_0\right\|^2 + \\ CS(\mu(E_i), \mu(E_i), \ldots, \mu(E_{EM})) \end{bmatrix} \quad (13)$$

where CS(·) represents the constraints on images from priori information in the compressive sensing framework.

Due to the correlation among spectral dependent attenuation coefficients and image sparsity, a PRISM algorithm, as disclosed by Gao, H., Yu, H., Osher, S. & Wang G. 2011, *Multi-energy CT based on a prior rank, intensity and sparsity model (PRISM)* Inverse problems, 27, 115012 (http://www.ncbi.nlm.nih.gov/pmc/articles/PMC2349839/) the entirety of which is incorporated herein by reference may be used to reconstruct the hybrid spectral CT as follows:

$$\operatorname*{argmin}_{\mu(E_j)} \left\{ \begin{array}{l} \sum_{j=1}^{EM} c_j \|A_c \mu(E_j) - Y_j\|^2 + \\ c_0 \left\|A_g\left(\sum_{j=1}^{EM} G_j \mu(E_j)\right) - Y_0\right\|^2 + \\ \lambda_1 LowRank(\mu(E_1), \mu(E_2), \ldots, \mu(E_{EM})) + \\ \lambda_2 TV(\mu(E_1), \mu(E_2), \ldots, \mu(E_{EM})) \end{array} \right\} \quad (14)$$

Note that there could be other PRISM variants as well. Next, the following variables may be used:

$$X_k = \mu(E_k), X = \{X_k, k \leq EM\}, y = \{Y_k, k \leq EM\}, Y_k = AX_k$$
$$\text{and } y = AX \quad (15)$$

The reconstruction of spectral dependent attenuation coefficients is reduced to the following optimization problem:

$$\operatorname*{argmin}_{X} \left\{ \|AX - y\|^2 + c_0 \left\|A_G \sum_{j=1}^{EM} G_j X_j - Y_0\right\|^2 + \lambda_1 |X|_* + \lambda_2 |TV(X)|_1 \right\} \quad (16)$$

This optimization problem may be solved using the split-Bregman method set forth in Chu, J., Li, L., Chen, Z., Wang, G., & Gao, H. 2012. *Multi-Energy CT Reconstruction Based on Low Rank and Sparsity with the Split-Bregman Method* (MLRSS). 2012 IEEE Nuclear Science Symposium and Medical Imaging Conference Record (NSS/MIC), M09-42, pp. 2411-2414, the entirety of which is incorporated herein by reference.

Set forth below is an algorithm to solve Eq. (16):

---

Algorithm 1: Algorithm to solve Eq. (16)

Step 1. Denote the variables $D = X$, $B_1 = \frac{\partial}{\partial i} X$, $B_2 = \frac{\partial}{\partial j} X$ Step 2. Define $V, W_1, W_2$ to represent the differences:

$$\operatorname*{argmin}_{X} \|\mathcal{A}(X) - \mathcal{Y}\|_2^2 + c_0 \left\|A_G \sum_{j=1}^{3} G_j X_j - Y_0\right\|^2 + \lambda_1 |D|_* + \mu_1 \|D - X - V\|_2^2 +$$

$$\lambda_2 (|B_1|_1 + |B_2|_1) + \mu_2 \left( \left\|B_1 - \frac{\partial}{\partial i} X - W_1\right\|_2^2 + \left\|B_2 - \frac{\partial}{\partial j} X - W_2\right\|_2^2 \right)$$

-continued

Algorithm 1: Algorithm to solve Eq. (16)

Step 3. Set the initial value $\mathcal{X}^0 = D^0 = V^0 = B_1^0 = B_2^0 = W_1^0 = W_2^0 = 0$
Step 4. Perform the following tasks until one of the stopping criteria $$\left(t = t_{end} \text{ or } \frac{\|\mathcal{X}^t - \mathcal{X}^{t-1}\|}{\|\mathcal{X}^{t-1}\|} \leq \epsilon\right) \text{ is met.}$$

$$\mathcal{X}^{t+1} = \operatorname{argmin}_{\mathcal{X}} \|\mathcal{A}(\mathcal{X}) - \mathcal{Y}\|_2^2 + c_0 \left\|A_G \sum_{j=1}^{3} G_j X_j - Y_0\right\|^2 + \mu_1 \|\mathcal{D}^t - \mathcal{X} - $$

$$V^t\|_2^2 + \mu_2 \|B_1^t - \partial\partial i\mathcal{X} - W_1^t\|_2^2 + \|B_2^t - \partial\partial j\mathcal{X} - W_2^t\|_2^2$$

$$D^{t+1} = \operatorname{argmin}_D \mu_1 \|D - X^{t+1} - V^t\|^2 + \lambda_1 |D|^*$$

$$V^{t+1} = V^t + \mathcal{X}^{t+1} - D^{t+1}$$

$$B_1^{t+1} = \operatorname{argmin}_{B_1} \mu_2 \left\|B_1 - \frac{\partial \mathcal{X}^{t+1}}{\partial i} - W_1^t\right\|_2^2 + \lambda_2 |B_1|_1$$

$$B_2^{t+1} = \operatorname{argmin}_{B_2} \mu_2 \left\|B_2 - \frac{\partial \mathcal{X}^{t+1}}{\partial j} - W_2^t\right\|_2^2 + \lambda_2 |B_2|_1$$

$$W_1^{t+1} = W_1^t + \frac{\partial}{\partial i} \mathcal{X}^{t+1} - B_1^{t+1}$$

$$W_2^{t+1} = W_1^t + \frac{\partial}{\partial j} \mathcal{X}^{t+1} - B_2^{t+1}$$

Each of the above steps is solvable in polynomial time using available methods such as set forth in (C et al., 2012) above.

When an object is large, there is a nonlinear relation of Eq. (5) between the spectrally dependent coefficients $\mu_i(E_j)$ at energy $E_j(j=1, 2, \ldots, EM)$ and measured grayscale data $I_{gray}$.

The image reconstruction for spectral CT can be formulated as the following nonlinear optimization problem:

$$\operatorname*{argmin}_{\mu(E_i)} \left[ \sum_{j=1}^{EM} c_j \|A_c \mu(E_j) - Y_j\|^2 + CS(\mu(E_1), \mu(E_1), \ldots, \mu(E_{EM})) \right] \quad (17)$$

$$\text{s.t. } I_{gray} = \sum_{j=1}^{EM} Q_j I_0(E_j) \exp\left(-\sum_{i=1}^{N} w_i \mu_i(E_j)\right)$$

where $CS(\cdot)$ represents the constraints on images from priori information in the compressive sensing framework. This optimization can be solved using a nonlinear Conjugate gradient or quasi Newton methods. Generally speaking, the computational time will be longer with a more general object model. Nevertheless, the same imaging principle applies.

Another embodiment of the present invention provides an innovative device and method to perform spectral CT imaging using a spectral detector module with controllable threshold(s) to define two or more energy bins or windows dynamically. A full-length detector array may consist of such modules. The energy ranges defined by the thresholds can be implemented by setting reference voltages. This allows for the counting of x-ray falling in one of the defined energy windows. In one embodiment, dynamically changing threshold may be used to perform dual-energy detection.

In another embodiment, two adaptive thresholds to define three energy window, one of which may be narrow, is provided. Another implementation of the invention is to provide diversified energy thresholds within a detector array and to keep them intact during scanning. The thresholds may also be dynamically changeable and or spatially different from detector to detector. In addition, the thresholds may be spatially different form one or more photon counting detector elements to one or more photon counting detector elements.

The dynamic thresholding scheme allows spectral characteristics to be sensed in a random fashion. Such data can be reconstructed into spectral images in a compressive sensing framework. By doing so, energy windowing can be done in a retrospective fashion. Hence, spatially varying optimization of energy windows becomes possible.

The image reconstruction algorithm described above may be used to handle dynamically thresholded data in the ease of a relatively small or weakly attenuating object. The only difference lies in that the number of energy windows is relatively small, such as 2 or 3, and the energy window settings may change from it detector to detector, and from view to view.

To evaluate the embodiments described above, a thorax-like phantom, FIG. 2, was employed, that is the Forbild thorax phantom defined on http://www.imp.uni-erlangen.de/forbild. The phantom of 20 cm×20 cm was sealed down to make the linear approximation Eq. (9) valid, and discretized into a 256×256 spatial grid, with a pixel size of 0.078125 cm. This leads to a linear system in the form of Eq. (11). The task then becomes the inversion of the system Eq. (11) by solving the objective function Eq. (16) using the above-described split-Bregman Algorithm 1. The objects and attenuation coefficients are detailed in FIG. 2, Table 1 and FIG. 3.

TABLE 1

Figure 2:
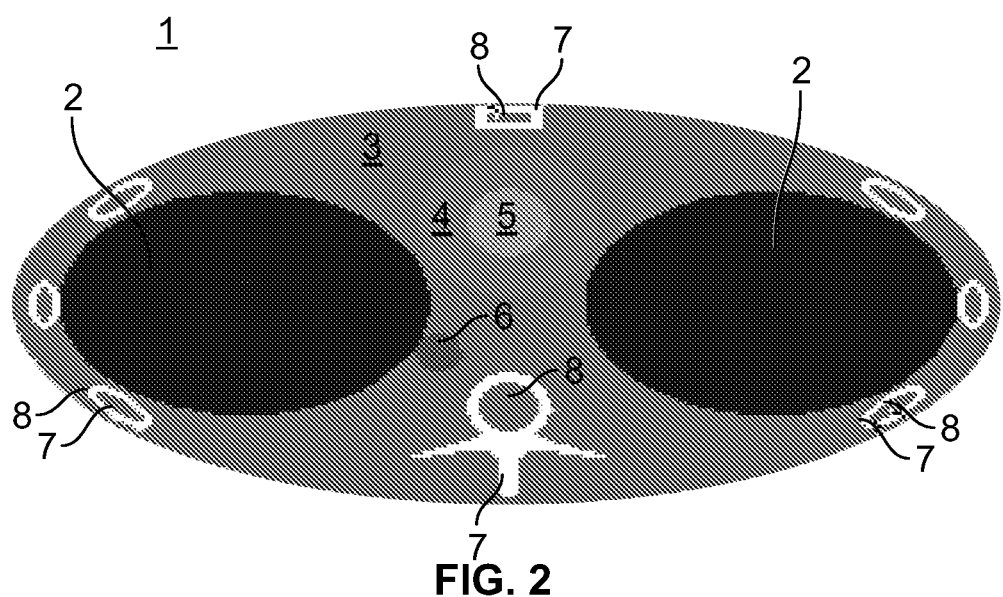
FIG. 2 shows the thorax phantom where the sub-regions are defined in Table 1.
Figure 3:
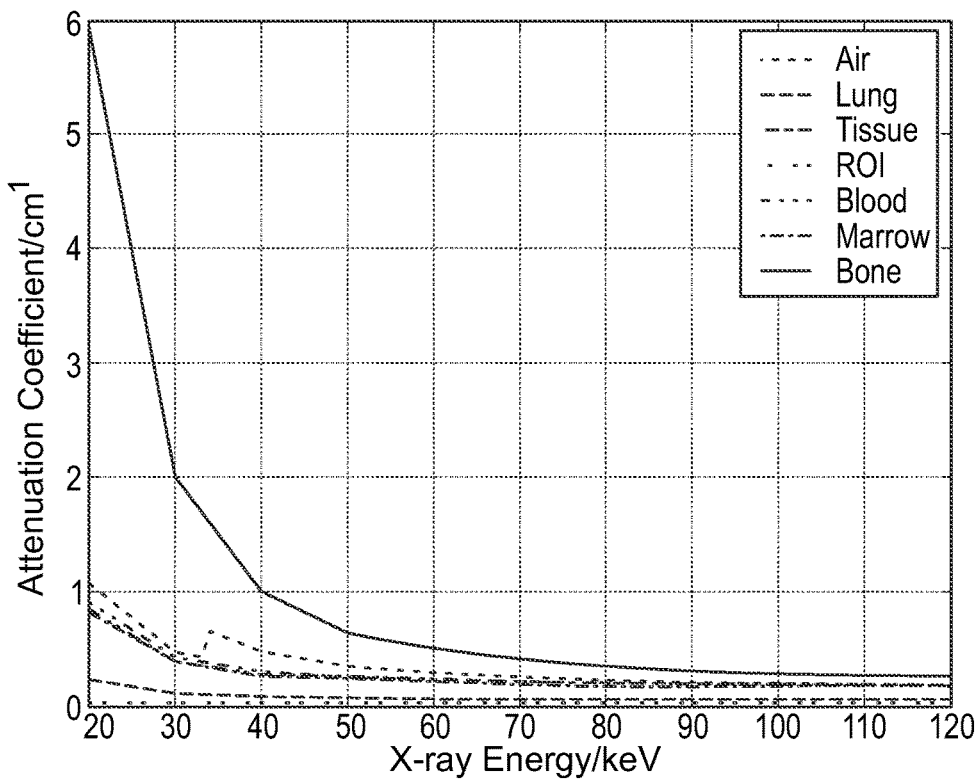
FIG. 3 shows the attenuation coefficient of the phantom materials. The ROI (region of interest) curve shows a K-edge at 33-34 keV for one embodiment of threshold levels that may be used with an embodiment of the invention.

Material types of the phantom sub regions shown in FIG. 2.

| Number | Material | Density (g/cm³) |
|---|---|---|
| 1 | Air | 0.00 |
| 2 | Lung | 0.26 |
| 3 | Tissue | 1.00 |
| 4 | Heart (Blood) | 1.06 |
| 5 | ROI (0.9% Iodine + 99.1% Blood) | 1.00 |
| 6 | Artery (Blood) | 1.06 |
| 7 | Bone | 1.50 |
| 8 | Marrow | 0.98 |

Figure 4:
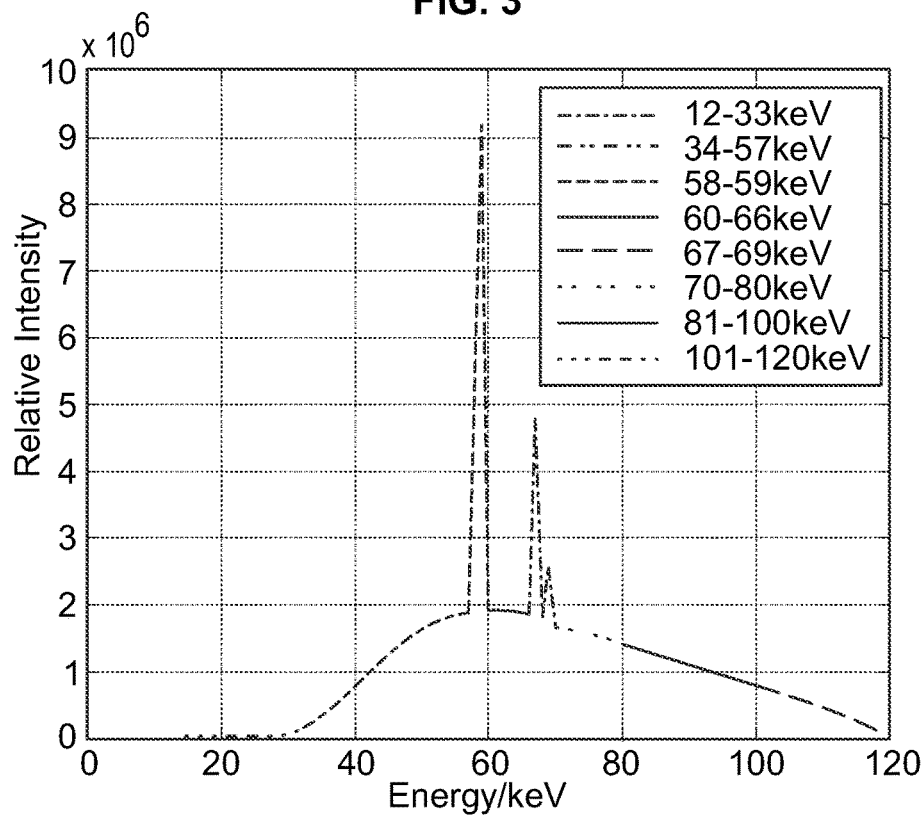
FIG. 4 shows the partition of the x-ray spectrum into 8 energy channels.

The x-ray spectrum was simulated assuming a 1.5 mm Al and 0.5 mm Cu filter, from 1 keV to 120 keV. In the simulation, the spectrum was discretized into 120 intervals, each of which may be 1 keV in length. With a Medipix detector, 8 energy Channels were measured and then combined to realistically simulate projection from 120 into 8 energy channels, as shown in FIG. 4.

Projection data was synthesized from the linear detector array of 256 elements via ray tracing, in a fan-beam geometry. Equi-angular 180 projections over a full scan were acquired. One simulation had no noise, and another one was corrupted by Gaussian noise to yield a signal-to-noise ratio of −20 dB in the projects. The basic parameters are indicated in Table 2.

TABLE 2

Nominal parameters of the imaging geometry before scaling down in the numerical simulation.

| Parameter | Value |
|---|---|
| Distance between the object and the x-ray source | 50 cm |
| Distance between the object and the detector array | 50 cm |
| Length of the detector array | 45 cm |
| Phantom side length | 20 cm |
| Pixel size | 0.078125 cm |
| Detector size | 0.1 cm |
| Number of detectors | 256 |
| Number of viewing angles | 180 |

An evenly alternating pattern, as shown in FIG. 1A, may be used for the detector modules to form a hybrid detector array. Various Pr values were studied, which is the ratio between the number of the grayscale elements and the number of spectral elements. A recursive method was used to find an optimal Pr. Pr from 1, 2, 3 . . . to 20 were tested, and image reconstruction was performed with sufficient iterations. For a specific ratio Pr, both the peak signal-to-noise ratio (PSNR) was calculated to obtain the structural similarity index measure (SSIM) between the true phantom image and the reconstructed image.

Given a reference image f and a test image g, both of M×N, the PSNR between f and g is defined as:

$$PSNR(f, g) = 10 \log_{10}\left(\frac{255^2 MN}{\sum_{i=1}^{M} \sum_{j=1}^{N} (f_{ij} - g_{ij})^2}\right) \quad (17)$$

A higher PSNR value is generally desirable. On the other hand. SSIM detects image distortion by combining three factors that are loss of correlation, luminance distortion and contrast distortion. The SSIM is defined as:

$$SSIM(f, g) = \frac{2\mu_f \mu_g + C_1}{\mu_f^2 + \mu_g^2 + C_1} \times \frac{2\sigma_f \sigma_g + C_2}{\sigma_f^2 + \sigma_g^2 + C_2} \times \frac{\sigma_{fg} + C_3}{\sigma_f \sigma_g + C_3} \quad (18)$$

$\mu_f$ and $\mu_g$ are the mean values, $\sigma_f$ and $\sigma_g$ are the standard deviations, $\sigma_{fg}$ is the covariance between f and g, $C_1$, $C_2$ and $C_3$ are constants to avoid null denominators. A higher SSIM value suggests a better image quality in a way complementary to PSNR.

Figure 5:
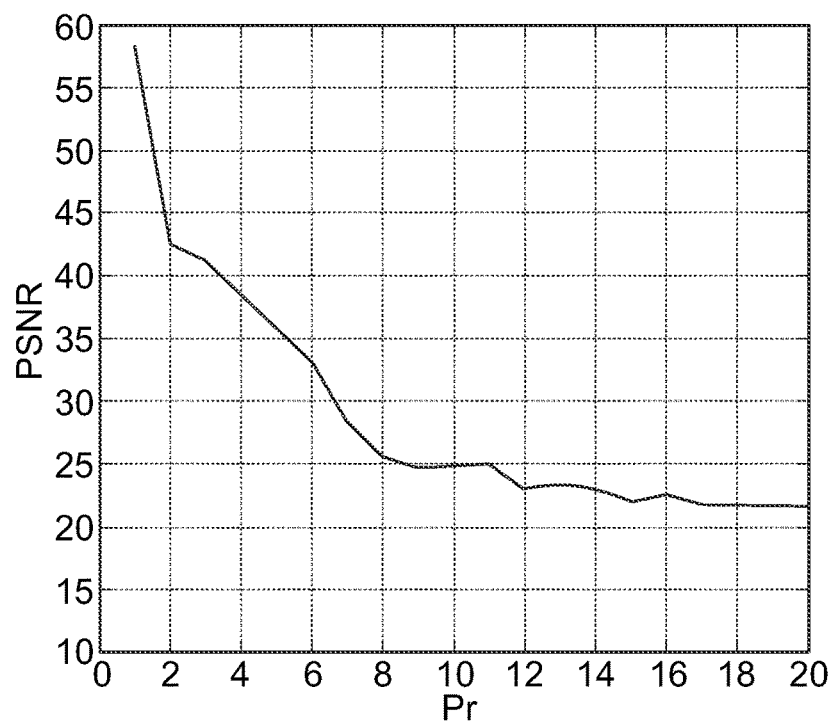
FIG. 5 shows PSNR as a function of Pr for the thorax phantom with no noise after 5 iterations.
Figure 6:
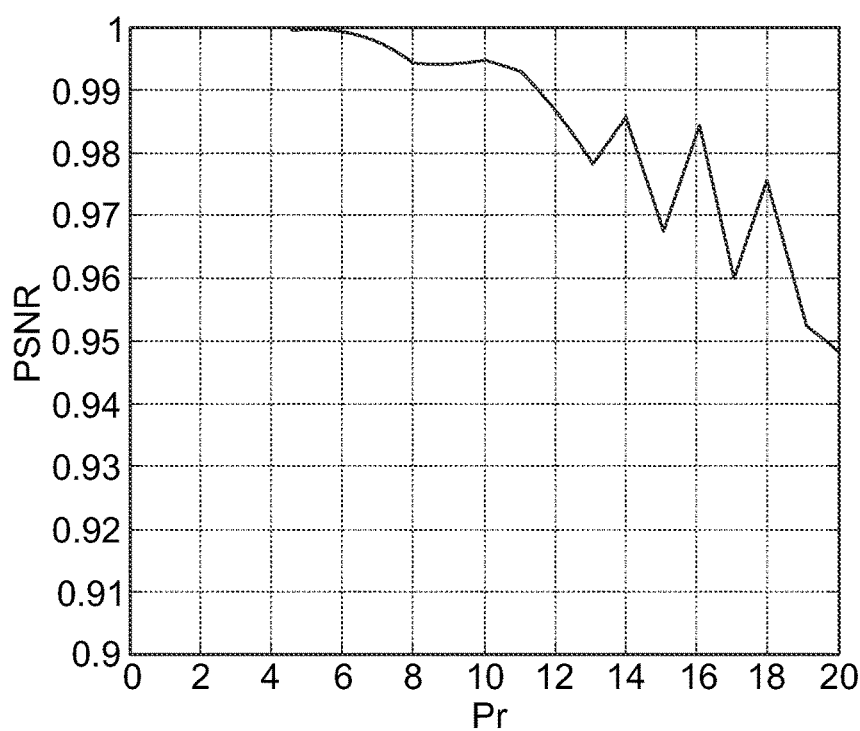
FIG. 6 shows SSIM as is function of Pr for the thorax phantom with no noise after 5 iterations.

FIGS. 5-6 provide PSNR and SSIM values as a function of Pr for the thorax phantom without noise. Generally, the more spectral elements there are, the better image quality is. For an iterative method, performing more iterations will normally improve the image quality. Using a Split-Bregman iterative reconstruction, 5 iterations were found to provide sufficient and adequate image quality.

Figure 7A:
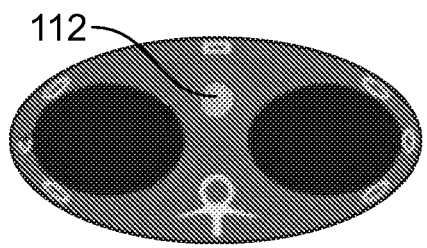
FIG. 7A shows the original image.
Figure 7B:
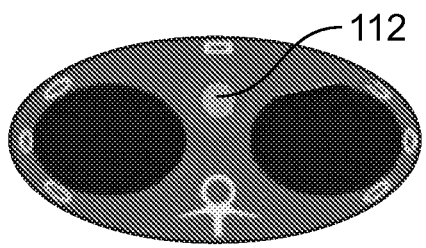
FIG. 7B shows a reconstructed image from noise-free data at Pr=1.
Figure 7C:
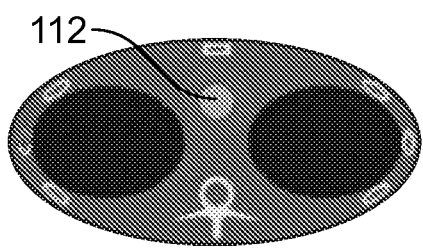
FIG. 7C shows a reconstructed image from noise-free data at Pr=3.
Figure 7D:
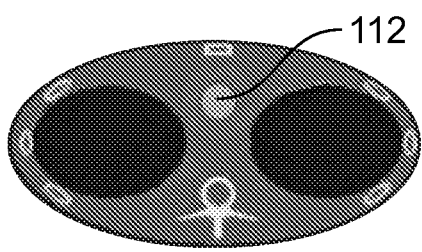
FIG. 7D shows a reconstructed image from noise-free data at Pr=5.
Figure 7E:
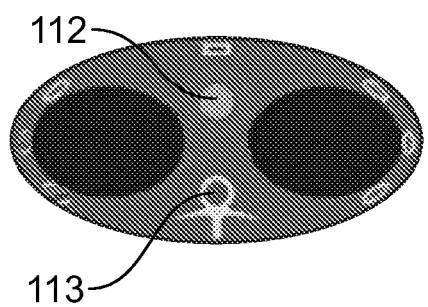
FIG. 7E shows a reconstructed image from noise-free data at Pr=7.
Figure 7F:
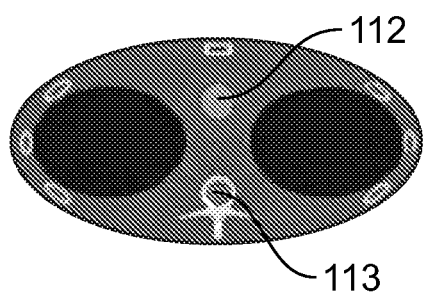
FIG. 7F shows a reconstructed image from noise-free data at Pr=9.
Figure 7G:
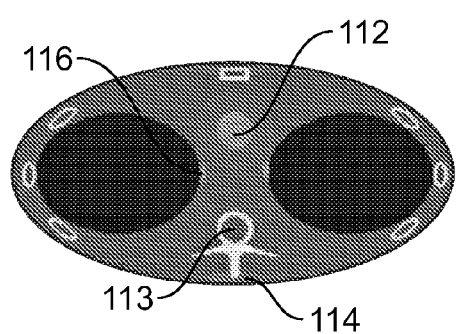
Figure 7H:
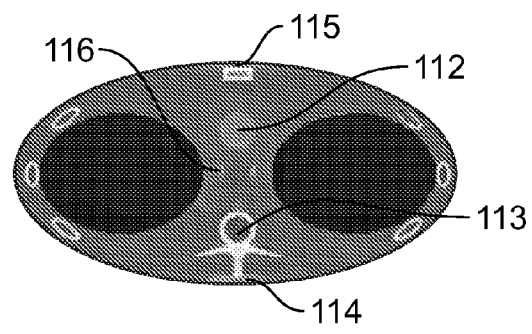
Figure 8:
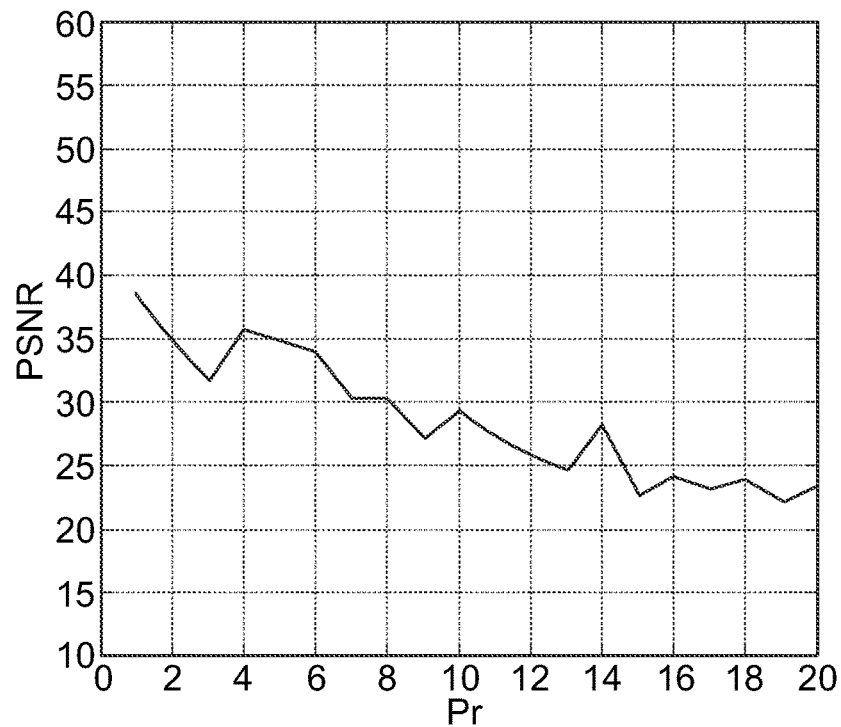
FIG. 8 shows PSNR as a function of Pr for the thorax phantom with noise after 5 iterations.
Figure 9:
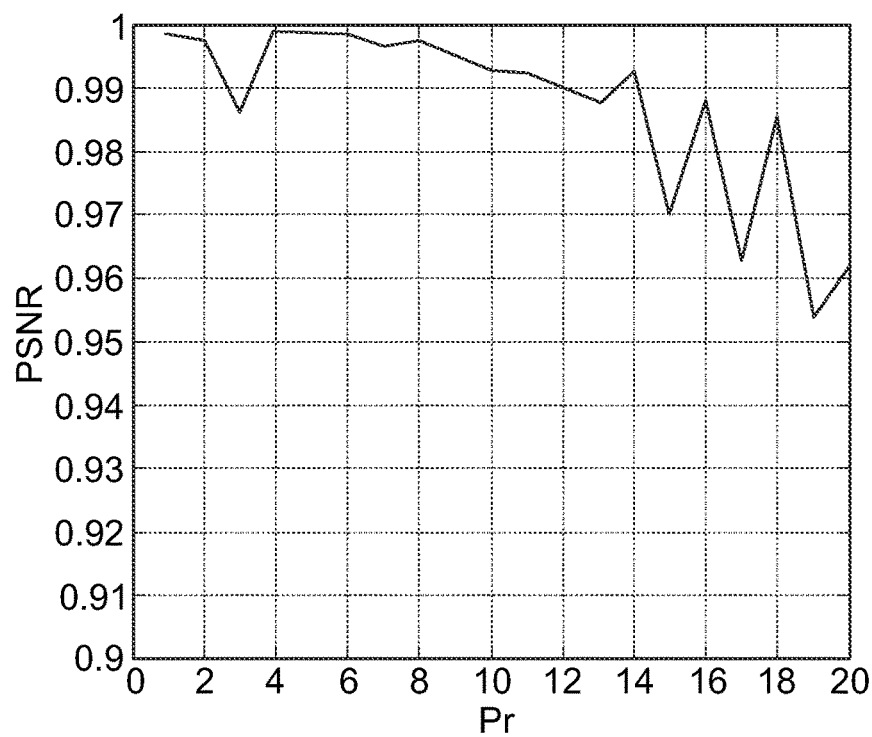
FIG. 9 shows SSIM as a function of Pr for the thorax phantom with noise after 5 iterations
Figure 10G:
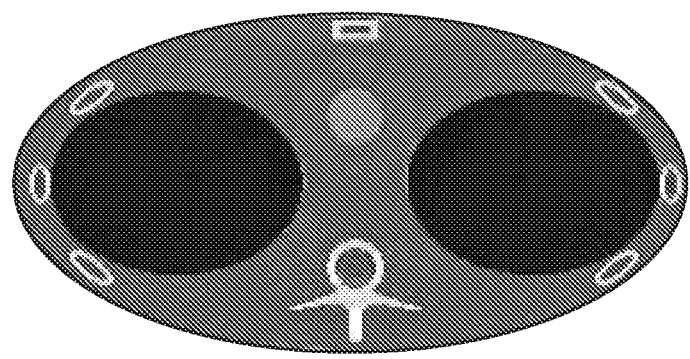
FIG. 10G shows a reconstructed image from noise-free data at Pr=11.
Figure 10H:
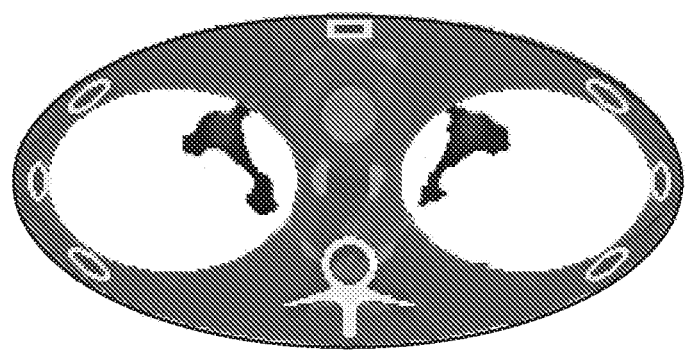
FIG. 10H shows a reconstructed image from noise-free data at Pr=13.

FIGS. 7A-7H present the original and reconstructed thorax phantom without noise for Pr=1, 3, 5, 7, 9, 11, 13. The image window is from 0 to the largest value in the original image. FIG. 7A shows the original image which has poor colors and sharp edges. The colors are based on 8 energy channels. Areas 112-116 represent regions of interest ("ROI").

From the profiles and images, it can be seen that for Pr<9 the SSIM is larger than 0.99, which we consider acceptable. Note that when Pr is large (>11), the ROI region will be blurry, and some "ghosts" may appear due to the lack of spectral detectors.

FIGS. 8 and 10A-10H show similar results with the thorax phantom and noisy data (SNR=20 dB). From the projection data with Poisson noise, good images (SSIM>0.99) were still obtained over the ROI in the cases of Pr<9.

Figure 11:
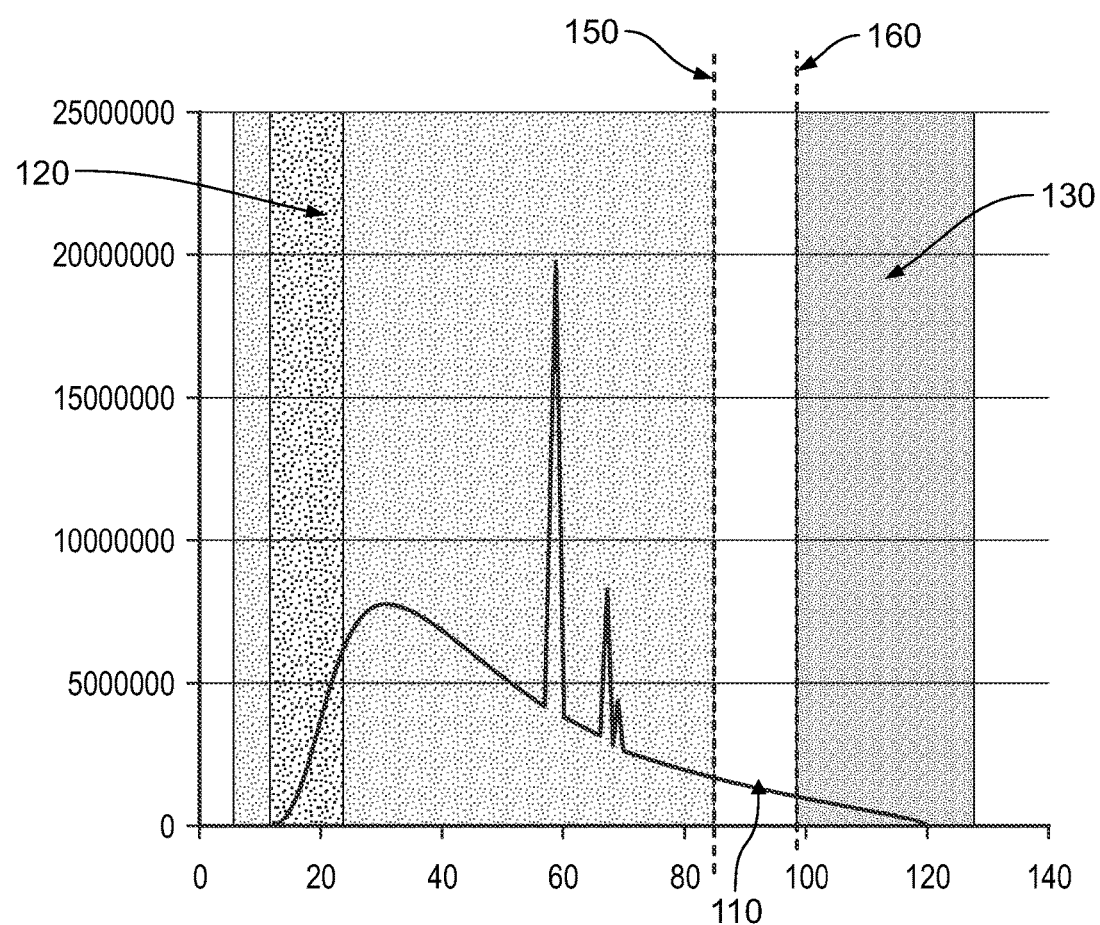
FIG. 11 is a schematic illustrating dynamic triple energy windows, with energy windows on the left, middle, and right respectively.
Figure 12A:
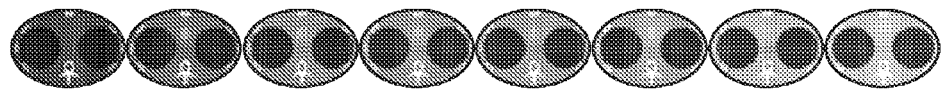
FIGS. 12A and 12B show representative results reconstructed from dynamic thresholding into 3 energy windows and fixed thresholding into 8 energy windows (Medipix setting).
Figure 12B:
Figure 13:
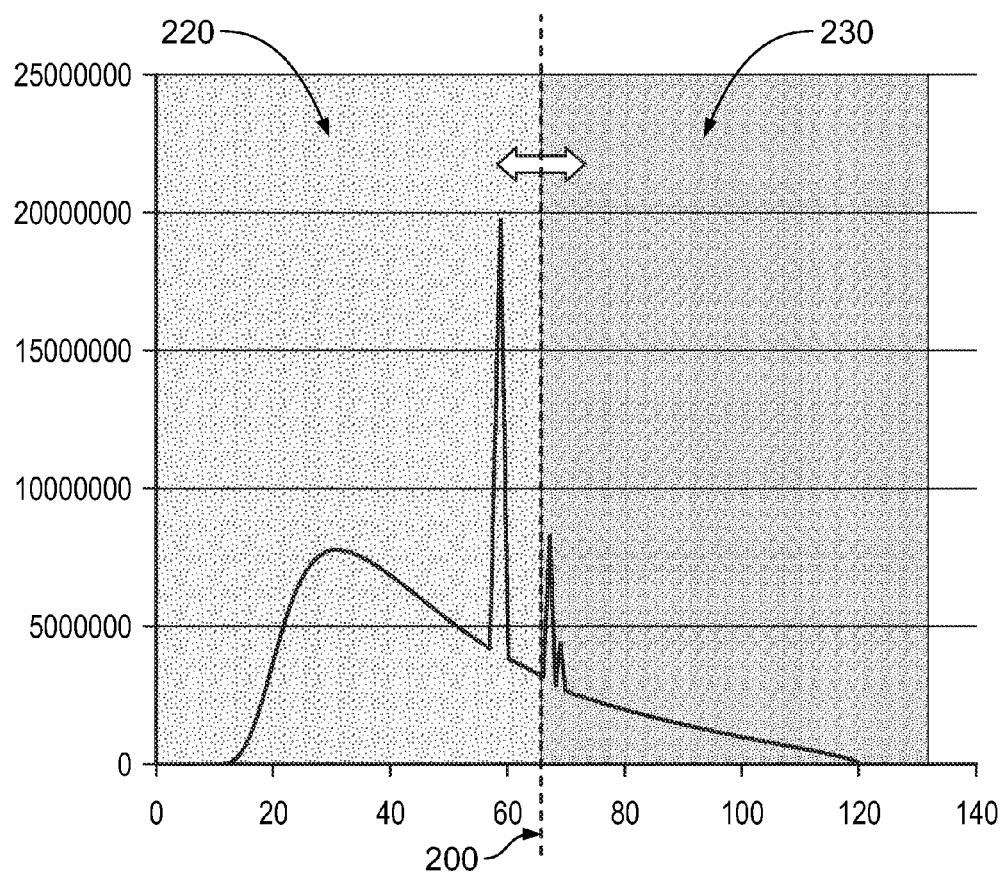
FIG. 13 depicts spectral regions covered by a dual-energy-window detector element.
Figure 14A:
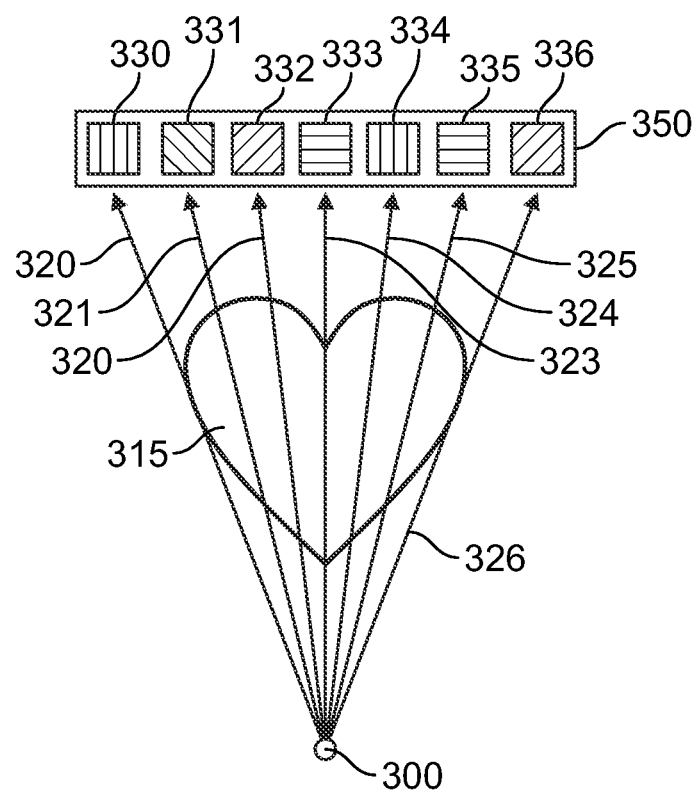
FIG. 14A depicts a detector arrangement that may be used by an embodiment of the invention.
Figure 14B:
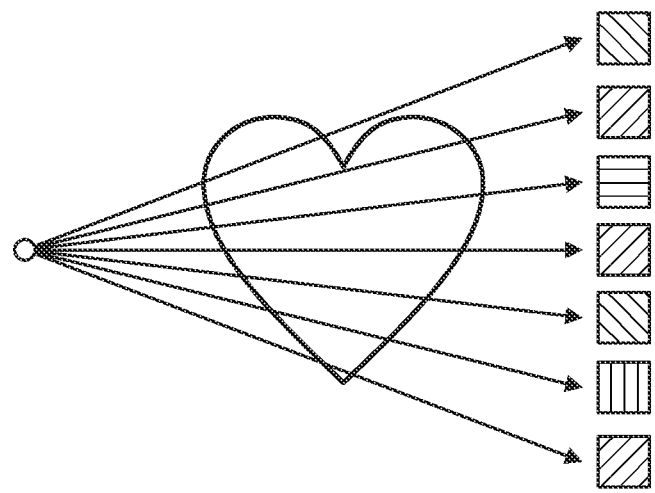
FIG. 14B shows the detector arrangement of FIG. 14A at a different orientation.
Figure 14C:
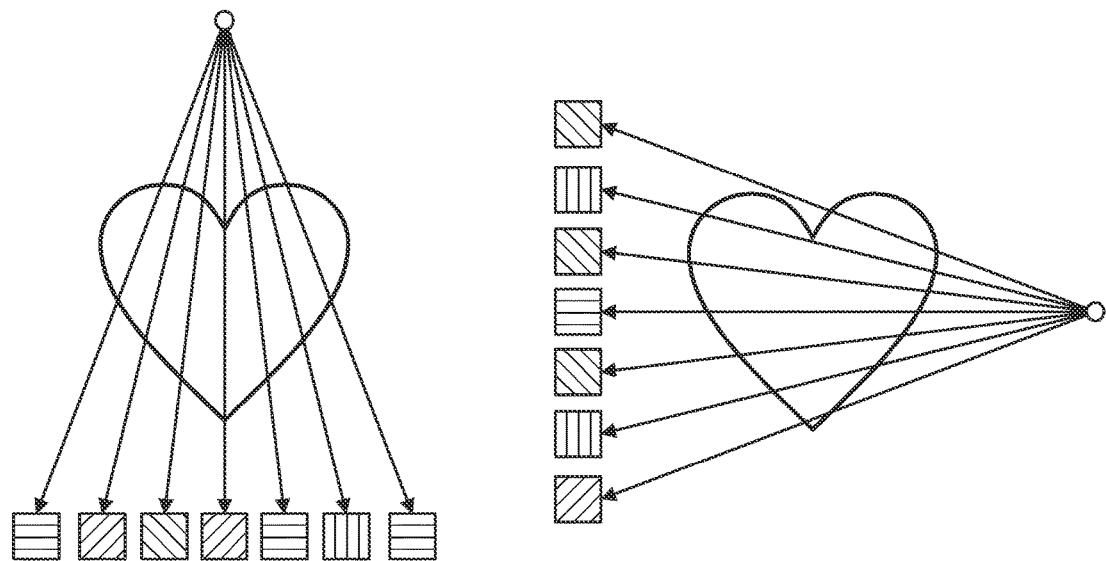
FIG. 14C shows the detector arrangement of FIG. 14A at a different orientation.
Figure 14D:
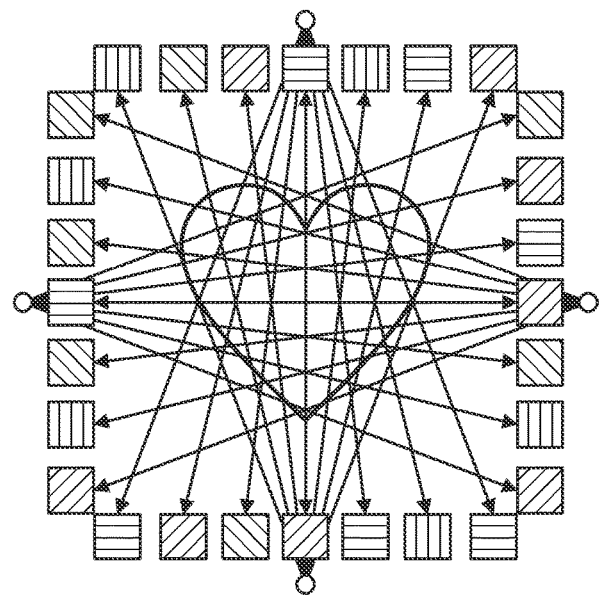
FIG. 14D shows the detector arrangement of FIG. 14A at a different orientation.

Numerical simulation was also performed for spectral CT with a dynamic thresholding scheme such as is shown in FIGS. 11 and 14A-14D. A representative study is presented in FIGS. 12A-12B (in the same simulation conditions described above, except for different thresholding schemes), which show that dynamically configuring the detector to use 3 dynamic energy windows or thresholds allows similar spectral CT reconstruction in 8 fixed energy windows (which is the Medipix setting). The 3 dynamic energy windows may be configured as shown in FIG. 11 which illustrates a tri-value detector that has 3 dynamically changeable photon counting regions, bins, areas or windows. The first area, region, bin or window 110 is established and bounded by a first energy level 150 and a second energy level 160. Second area, region, bin or window 120 is bounded by energy levels that are lower than first energy level 150. A third area, region, bin or window 130 represents energy levels that are greater than second energy level 160. FIG. 13 shows yet another embodiment providing dual-energy-window detector elements, in this embodiment, threshold 200 is used and defines a first photon counting region, bin, area or window 220 and a second 230. As stated, the thresholds and corresponding windows may be dynamically changed. In addition, 2, 3 or more windows may be used as well as additional windows depending on the number of energy channels desired.

Counting photons in a window and out of to window generates projection data. The window can be changed randomly during scanning, and different detectors may have different windows in different angles. Each position of the window is an energy channel. This results in the creation of a complex system matrix; utilizing the relationship among different energy channels, it is possible to reconstruct images in high quality.

As shown in FIGS. 14A-14D, the system and method comprise an X-ray source 300 configured to emit an X-ray beam 320-326; an object positioned to receive the X-ray beam 315; a detector 350 configured to receive an attenuated beam of the X-rays through the object for measuring projection data from various orientations that can be used to generate spectral images in terms of energy-dependent linear attenuation coefficients. The detector, as described above, comprises one or more energy-integrating detector elements 330, 331, and 333-335 and one or more photon counting detector elements 132 and 336 in one or more detector arrays or separate detector arrays.

In addition, the detectors described above may be arranged such that different detectors have differ it windows at different angles, which may be randomly selected as shown in FIGS. 14A-14D. As shown, various orientations may be deployed and even encircle an object. Accordingly, in one preferred embodiment, the above-described teachings may be used to configure an energy-sensitive or spectral computed tomography system for use in the applications described above such as in applications herein the object comprises a human being, an animal, baggage, a specimen, industrial part.

The system may further be configured such that the energy-integrating detector elements and the photon counting detector elements arranged in alternating, merged, centered or random patterns. The system may use a ratio where the number of energy-integrating elements and said photon counting elements is no more than 11 to 1.

Other configurations include photon counting elements including two, three or more thresholds including embodiments where of or more thresholds define one or more windows and the one more photon counting elements count the photons in the window or windows and out of the window or windows. The thresholds and corresponding windows may be dynamically changeable as desired and the windows may have different orientations such as having windows at different angles with the viewing angles being 360 in some embodiments so as to encircle an object.

The above described system and method may be configured to further comprise a detector module operable configured for receiving localized projection data through a region of interest (ROI); reconstructing the ROI into a spectral image from local spectral data, with or without an individualized grayscale reconstruction of an entire field of view, including the ROI. An algorithm for image reconstruction that may be used with the system is the split-Bregman technique described above. Other algorithms and programs may be used as well such as iterative, non-iterative or optimization techniques for image reconstruction.

For another preferred system and method to perform energy-sensitive or spectral computed tomography, the above-described teachings may also be used in applications wherein the object comprises a human being an animal, baggage, a specimen or industrial part. The system and method comprising air X-ray source configured to emit an X-ray beam; an object positioned to receive the X-ray beam; one or more detectors configured to receive attenuated beam of the X-rays through the object for measuring projection data from various orientations that can be used to generate spectral images in terms it energy-dependent linear attenuation coefficients. The one or a more detectors comprise one or more detector elements with dynamically adjustable thresholds which may be one or more windows (for each detector element) or spatially randomized energy thresholds (along a detector array) to capture spectral information. The number of energy windows specified may be dynamically adjustable adjustable or randomized and 2-3 thresholds n be used for each detector element at a given time instant. above described system and method may be configured to further comprise a detector module operably configured for receiving localized projection data through a region of interest (ROI): reconstructing the ROI into a spectral image from local spectral data, with or without an individualized grayscale reconstruction of an entire field of view, including the ROI. An algorithm for image reconstruction that may be used with the system and method is the split-Bregman technique described above. Other algorithms and programs may be used as well such as iterative, non-iterative or optimization techniques for image reconstruction.

Other configurations for the above-described embodiment include photon-counting elements including one, two, three or more thresholds including embodiments where the threshold is a window and the photon counting elements count the photons in the window and out of the window or windows. The windows may be dynamically changeable as desired and the windows may have different orientations such as having windows at different angles with the viewing angles being 360 in some embodiments to encircle an object.

What is claimed is:

1. An energy-sensitive or spectral computed tomography system comprising:
   an X-ray source configured to emit X-ray beams at an object;
   one or more detectors configured to receive attenuated beams of the X-rays from an object for measuring projection data to generate spectral images in terms of energy-dependent linear attenuation coefficients; and
   said one or more detectors comprising one or more energy-integrating detector elements and one or more photon counting detector elements in one or more detector arrays; and
   at least one of said photon counting elements count the photons within a window and out of a window, and said window defined by one or more dynamically changeable thresholds to capture spectral information in one or more dynamically changeable windows, said windows defined by said thresholds during a scanning process.

2. The system of claim 1, wherein said projection data is received from a plurality of orientations to sample an object from different orientations using different energy thresholds.

3. The system of claim 1, wherein said elements are arranged in alternating, merged, centered or random patterns.

4. The system of claim 1, wherein the ratio of the number of said energy-integrating elements to said photon counting elements is no more than 11 to 1.

5. The system of claim 1, wherein said thresholds are spatially different from said photon counting detector element to said photon counting detector element.

6. The system of claim 1, wherein the system has one dynamically changeable threshold that defines two energy windows.

7. The system of claim 6, wherein image reconstruction is performed using polychromatic physical model.

8. The system of claim 1, wherein the system has two dynamically changeable thresholds that define three energy windows.

9. The system of claim 1, further including one or more detector modules operably configured to receive projection data through a region of interest (ROI); reconstructing the ROI into a spectral image, with or without an individualized grayscale reconstruction.

10. The system of claim 9, wherein the algorithm used for image reconstruction is the split-Bregman technique.

11. The system of claim 9, wherein image reconstruction is performed using iterative or non-iterative techniques.

12. An energy-sensitive or spectral computed tomography system comprising:
    an X-ray source configured to emit X-ray beams at an object;
    one or more detectors configured to receive attenuated beams of the X-rays from an object for measuring projection data to generate spectral images in terms of energy-dependent linear attenuation coefficients; and
    one or more detectors comprising one or more detector elements, said one or more detector elements having one or more dynamically changeable thresholds defining windows to capture spectral information in view dependent energy windows defined during scanning.

13. The system of claim 12, wherein one or more thresholds are used for each detector element at a given time instant.

14. The system of claim 12, wherein the system has one dynamically changeable threshold that defines two energy windows.

15. The system of claim 12, wherein the system has two dynamically changeable thresholds that define three energy windows.

16. The system of claim 12, further including one or more detector modules operably configured to receive projection data through a region of interest (ROI); reconstructing the ROI into a spectral image, with or without an individualized grayscale reconstruction.

17. The system of claim 16 wherein image reconstruction is performed using polychromtic physical model.

18. The system of claim 16, wherein the algorithm used for image reconstruction is the split-Bregman technique.

19. The system of claim 16, wherein image reconstruction is performed iteratively or non-iteratively.

20. The system of claim 12 wherein one or more detectors comprising one or more photon counting detector elements.

21. A radiation detector system, comprising:
    one or more detectors comprising one or more detector elements, said one or more detector elements having one or more dynamically changeable thresholds defining windows to capture spectral information in view-dependent energy-bins defined during scanning.

* * * * *